US008563731B2

(12) United States Patent  
Carrera et al.

(10) Patent No.: US 8,563,731 B2
(45) Date of Patent: Oct. 22, 2013

(54) MESYLATE SALT OF 5-(2-{[6-(2,2-DIFLUORO-2-PHENYLETHOXY)HEXYL]AMINO}-1-HYDROXYETHYL)-8-HYDROXYQUINOLIN-2(1H)-ONE AS AGONIST OF THE β2 ADRENERGIC RECEPTOR

(75) Inventors: Francesc Carrera Carrera, Barcelona (ES); Carlos Puig Duran, Barcelona (ES); Iolanda Marchueta Hereu, Barcelona (ES); Enrique Moyes Valls, Barcelona (ES)

(73) Assignee: Almirall, S.A., Barcelona (ES)

( * ) Notice: Subject to any disclaimer, the term of this patent is extended or adjusted under 35 U.S.C. 154(b) by 20 days.

(21) Appl. No.: 13/141,156

(22) PCT Filed: Dec. 15, 2009

(86) PCT No.: PCT/EP2009/008970
§ 371 (c)(1),
(2), (4) Date: Jun. 21, 2011

(87) PCT Pub. No.: WO2010/072354
PCT Pub. Date: Jul. 1, 2010

(65) Prior Publication Data
US 2011/0251234 A1 Oct. 13, 2011

(30) Foreign Application Priority Data

Dec. 22, 2008 (EP) ..................... 08382082

(51) Int. Cl.
*C07D 215/38* (2006.01)
(52) U.S. Cl.
USPC ....................................................... 546/159
(58) Field of Classification Search
USPC ......................................... 546/159; 514/312
See application file for complete search history.

(56) References Cited

U.S. PATENT DOCUMENTS

| 2,579,479 A | 12/1951 | Djerassi et al. |
| 2,837,464 A | 6/1958 | Nobile et al. |
| 2,897,216 A | 7/1959 | Oliveto et al. |
| 3,007,923 A | 11/1961 | Muller et al. |
| 3,053,865 A | 9/1962 | Metuchen et al. |
| 3,104,246 A | 9/1963 | Amiard et al. |
| 3,134,719 A | 5/1964 | Sheth et al. |
| 3,678,137 A | 7/1972 | Pfeiffer et al. |
| 3,929,768 A | 12/1975 | Brattsand et al. |
| 3,970,677 A | 7/1976 | Nishimura et al. |
| 3,975,391 A | 8/1976 | Nakagawa et al. |
| 3,983,233 A | 9/1976 | Brattsand et al. |
| 3,994,901 A | 11/1976 | Nakagawa et al. |
| 4,022,776 A | 5/1977 | Nakagawa et al. |
| 4,022,784 A | 5/1977 | Nakagawa et al. |
| 4,026,897 A | 5/1977 | Nakagawa et al. |
| 4,068,076 A | 1/1978 | Nakagawa et al. |
| 4,145,542 A | 3/1979 | Nakagawa et al. |
| 4,753,962 A | 6/1988 | Ainsworth et al. |
| 4,992,474 A | 2/1991 | Skidmore et al. |
| 4,997,986 A | 3/1991 | Mitchell et al. |
| 5,099,068 A | 3/1992 | Mitchell et al. |
| 5,109,023 A | 4/1992 | Mitchell et al. |
| 5,201,308 A | 4/1993 | Newhouse |
| 5,263,475 A | 11/1993 | Altermatt et al. |
| 5,283,262 A | 2/1994 | Mitchell et al. |
| 5,435,301 A | 7/1995 | Herold et al. |
| 5,482,934 A | 1/1996 | Calatayud et al. |
| 5,507,281 A | 4/1996 | Kuhnel et al. |
| 5,617,845 A | 4/1997 | Poss et al. |
| 5,685,294 A | 11/1997 | Gupte et al. |
| 6,541,669 B1 | 4/2003 | Moran et al. |
| 7,498,321 B2 | 3/2009 | Biggadike et al. |
| 7,964,615 B2 * | 6/2011 | Duran et al. ................... 514/312 |
| 8,178,679 B2 | 5/2012 | Matassa et al. |
| 8,242,177 B2 * | 8/2012 | Duran et al. ................... 514/652 |
| 8,283,342 B2 * | 10/2012 | Duran et al. ................... 514/171 |
| 2002/0055651 A1 | 5/2002 | Moran et al. |
| 2003/0136405 A1 | 7/2003 | Goede et al. |
| 2003/0153597 A1 | 8/2003 | Moran et al. |
| 2004/0059116 A1 | 3/2004 | Moran et al. |
| 2004/0167167 A1 | 8/2004 | Mammen et al. |
| 2005/0043337 A1 | 2/2005 | Rito et al. |
| 2005/0159448 A1 | 7/2005 | McKinnell et al. |
| 2005/0192316 A1 | 9/2005 | Moran et al. |
| 2005/0215590 A1 | 9/2005 | Brown et al. |
| 2005/0272769 A1 | 12/2005 | Linsell |
| 2006/0019991 A1 | 1/2006 | McKinnell et al. |
| 2006/0035931 A1 | 2/2006 | Chao et al. |
| 2006/0081246 A1 | 4/2006 | Goede et al. |
| 2006/0178410 A1 | 8/2006 | Moran et al. |

(Continued)

FOREIGN PATENT DOCUMENTS

DE  2 236 272  2/1973
DE  2 323 215  11/1973

(Continued)

OTHER PUBLICATIONS

International Search Report for International Application No. PCT/EP2009/008970, mailed Mar. 2, 2010.
U.S. Appl. No. 13/094,156, filed Apr. 26, 2011, Puig Duran et al.
U.S. Appl. No. 13/094,163, filed Apr. 26, 2011, Puig Duran et al.
U.S. Appl. No. 13/538,117, filed Jun. 29, 2012, Bach Taña et al.
U.S. Appl. No. 13/428,450, filed Mar. 23, 2012, Giulio Matassa et al.
Budesonide, Merck index, Monograph No. 01468 (2012).
Ciclesonide, Merck index, Monograph No. 02263 (2012).
Interview Summary dated Feb. 22. 2012, for U.S. Appl. No. 12/745,195.
Interview Summary dated Jun. 26, 2012, in U.S. Appl. No. 12/526,090.

(Continued)

*Primary Examiner* — D Margaret M Seaman
(74) *Attorney, Agent, or Firm* — Finnegan, Henderson, Farabow, Garrett & Dunner, LLP

(57) ABSTRACT

The present disclosure relates to a mesylate salt of 5-(2-{[6-(2,2-difluoro-2-phenylethoxy)hexyl]amino}-1-hydroxyethyl)-8-hydroxyquinolin-2(1H)-one as well as pharmaceutical compositions comprising them, and their use in therapy as agonists of the β2 receptor.

12 Claims, 1 Drawing Sheet

(56) References Cited

U.S. PATENT DOCUMENTS

| | | |
|---|---|---|
| 2006/0205949 A1 | 9/2006 | Dalziel et al. |
| 2007/0197536 A1 | 8/2007 | Dal Piaz et al. |
| 2009/0042933 A1 | 2/2009 | Duran et al. |
| 2009/0082378 A1 | 3/2009 | Puig Duran et al. |
| 2010/0093681 A1 | 4/2010 | Duran et al. |
| 2010/0168161 A1 | 7/2010 | Tanã et al. |
| 2010/0324000 A1 | 12/2010 | Matassa et al. |
| 2011/0028442 A1 | 2/2011 | Duran et al. |
| 2011/0251165 A1 | 10/2011 | Duran et al. |
| 2011/0251166 A1 | 10/2011 | Duran et al. |
| 2012/0004414 A1 | 1/2012 | Hereu et al. |
| 2012/0029014 A1 | 2/2012 | Ruf et al. |
| 2012/0040941 A1 | 2/2012 | Ruf et al. |

FOREIGN PATENT DOCUMENTS

| | | |
|---|---|---|
| DE | 2 310 140 | 9/1974 |
| DE | 2 461 861 | 8/1975 |
| DE | 41 29 535 | 3/1992 |
| DE | 4 239 402 | 5/1994 |
| EP | 0 057 401 | 8/1982 |
| EP | 0 069 715 | 1/1983 |
| EP | 0 147 719 | 7/1985 |
| EP | 0 166 294 | 1/1986 |
| EP | 0 286 242 | 10/1988 |
| EP | 0 317 206 | 5/1989 |
| EP | 0 424 790 | 5/1991 |
| EP | 0 505 321 | 9/1992 |
| EP | 0 674 533 | 10/1995 |
| EP | 1 078 629 | 2/2001 |
| EP | 1 235 787 | 9/2002 |
| EP | 1 577 291 | 9/2005 |
| ES | 2 232 306 | 5/2005 |
| GB | 0 869 511 | 5/1961 |
| GB | 1 200 886 | 8/1970 |
| GB | 1 247 370 | 9/1971 |
| GB | 1 458 251 | 12/1976 |
| GB | 1 468 156 | 12/1976 |
| GB | 2 041 763 | 9/1980 |
| GB | 2 140 800 | 12/1984 |
| GB | 2 160 863 | 1/1986 |
| GB | 2 165 159 | 4/1986 |
| GB | 2 242 134 | 9/1991 |
| JP | 51 149 282 | 12/1976 |
| JP | 59 093 051 | 5/1984 |
| WO | WO 91/02558 | 3/1991 |
| WO | WO 91/14468 | 10/1991 |
| WO | WO 92/00771 | 1/1992 |
| WO | WO 92/03175 | 3/1992 |
| WO | WO 92/04068 | 3/1992 |
| WO | WO 92/04928 | 4/1992 |
| WO | WO 92/09322 | 6/1992 |
| WO | WO 96/32150 | 10/1996 |
| WO | WO 97/00703 | 1/1997 |
| WO | WO 97/12687 | 4/1997 |
| WO | WO 98/09632 | 3/1998 |
| WO | WO 99/30703 | 6/1999 |
| WO | WO 99/64035 | 12/1999 |
| WO | WO 01/36375 | 5/2001 |
| WO | WO 01/042193 | 6/2001 |
| WO | WO 02/066422 | 8/2002 |
| WO | WO 02/070490 | 9/2002 |
| WO | WO 02/092606 | 11/2002 |
| WO | WO 03/000325 | 1/2003 |
| WO | WO 03/042160 | 5/2003 |
| WO | WO 03/061742 | 7/2003 |
| WO | WO 03/072539 | 9/2003 |
| WO | WO 03/091204 | 11/2003 |
| WO | WO 03/097613 | 11/2003 |
| WO | WO 03/099764 | 12/2003 |
| WO | WO 04/011416 | 2/2004 |
| WO | WO 04/016578 | 2/2004 |
| WO | WO 2004/011416 | 2/2004 |
| WO | WO 2004/016578 | 2/2004 |
| WO | WO 2004/058729 | 7/2004 |
| WO | WO 2004/089892 | 10/2004 |
| WO | WO 2004/106279 | 12/2004 |
| WO | WO 2005/030678 | 4/2005 |
| WO | WO 2005/049581 | 6/2005 |
| WO | WO 2005/121065 | 12/2005 |
| WO | WO 2005/123692 | 12/2005 |
| WO | WO 2005/123693 | 12/2005 |
| WO | WO 2006/023457 | 3/2006 |
| WO | WO 2006/051375 | 5/2006 |
| WO | WO 2006/122788 | 11/2006 |
| WO | WO 2007/124898 | 11/2007 |
| WO | WO 2008/046598 | 4/2008 |
| WO | WO 2008/095720 | 8/2008 |
| WO | WO 2009/068177 | 6/2009 |
| WO | WO 2009/106351 | 9/2009 |
| WO | WO 2010/094483 | 8/2010 |
| WO | WO 2010/094484 | 8/2010 |
| WO | WO 2010/102831 | 9/2010 |

OTHER PUBLICATIONS

Mometasone, Merck Index, Monograph No. 06241 (2012).
Notice of Allowance dated Dec. 26, 2011 in U.S. Appl. No. 12/745,195.
Notice of Allowance dated Feb. 24, 2012 in U.S. Appl. No. 12/745,195.
Notice of Allowance dated Apr. 18, 2012, in U.S. Appl. No. 13/094,156.
Notice of Allowance dated Jun. 26, 2012, in U.S. Appl. No. 12/526,090.
Office Action (Restriction Requirement) dated Jul. 6, 2012 in U.S. Appl. No. 13/094,163.
Office Action dated Aug. 20, 2012, in U.S. Appl. No. 13/094,163.
Office Action (Restriction Requirement) dated Dec. 29, 2011 in U.S. Appl. No. 13/094,156.
Office Action dated Jan. 26, 2012 in U.S. Appl. No. 12/298,131.
Office Action dated Jan. 30, 2012 in U.S. Appl. No. 12/444,935.
Office Action (Quayle Action) dated Feb. 14, 2012, in U.S. Appl. No. 13/094,156.
Office Action dated Apr. 24, 2012, in U.S. Appl. No. 12/526,090.
Office Action (Advisory Action) dated Jun. 4, 2012, in U.S. Appl. No. 12/444,935.
Prednisone, Merck Index, Monograph No. 07722 (2012).
U.S. Appl. No. 11/920,561, filed Feb. 11, 2008, Puig Duran et al.
U.S. Appl. No. 12/298,131, filed Oct. 22, 2008, Puig Duran et al.
U.S. Appl. No. 12/444,935, filed Apr. 9, 2009, Bach Tana et al.
U.S. Appl. No. 12/526,090, filed Oct. 9, 2009, Puig Duran et al.
U.S. Appl. No. 12/745,195, filed May 27, 2010, Giulio Matassa et al.
U.S. Appl. No. 12/919,134, filed May 27, 2010, Giulio Matassa et al.
U.S. Appl. No. 13/202,020, filed Aug. 17, 2011, Ruf et al.
U.S Appl. No. 13/202,025, filed Aug. 17, 2011, Ruf et al.
Bastin, R. J. et al., "Salt selection and optimisation procedures for pharmaceutical new chemical entities," *Organic Process Research and Development*, 4(5):427-435 (2000).
Caplus English Abstract of DE 2 236 272, Accession No. 1973:405128.
Caplus English Abstract of DE 2 310 140, Accession No. 1975:31115.
Caplus English Abstract of JP 51 149 282, Accession No. 1977:468184.
Caplus English Abstract of JP 59 093 051, Accession No. 1985:45790.
Caplus English Abstract of journal article by Meglio, P. et al. Accession No. 1980:426036.
Coleman, R.A. et al., "Novel and versatile superfusion system," *Journal of Pharmacological Methods*, 21:71-86 (1989).
Curran, P.K. et al., "Endogenous $\beta_3$-but not $\beta_1$-adrenergic receptors are resistant to agonist-mediated regulation in human SK-N-MC neurotumor cells," *Cell. Signa.*, 8(5):355-364 (1996).
Deyrup, M.D. et al., "Structure-affinity profile of 8-hydroxycarbostyril-based agonists that dissociate slowly from the $\beta_2$-adrenoceptor," *Naunyn-Schmiedeberg's Archives of Pharmacology*, 359:168-177(1999).

(56) References Cited

OTHER PUBLICATIONS

Han, J., "Advances in characterization of pharmaceutical hydrates," *Trends in Bio/Pharmaceutical Industry*, 3:25-29 (2006).
Hart, D.J. et al., "Total syntheses of dl-gephyrotoxin and dl-dihydrogephyrotoxin," *J. American Chem. Society*, 105(5)1255-1263 (1983).
Hashima, H. et al.,"Synthesis and biological activities of the marine byrozoan alkaloids convolutamines A, C and F, and lutamides A and C," *Bioorganic & Medicinal Chemistry*, 8:1757-1766 (2000).
Hett, R. et al., "Large-scale synthesis of enantio- and diastereomerically pure (R,R)-formoterol," *Organic Process Research & Development*, 2(2):96-99 (1998).
Ismail, F.M.D., "Important fluorinated drugs in experimental and clinical use," *Journal of Fluorine Chemistry*, 118:27-33 (2002).
de Meglio, P. et al., "Synthesis and pharmacological study of orciprenaline and salbutamol derivatives," *Farmaco, Edizione Scientifica*, 35(3):203-230 (1980).
Meyers, A.I. et al., "Substitutions on 1-methoxynaphthalenes via their oxazoline derivatives: a convenient route to 1-substituted naphthoic acids," *Synthesis Communications*, 2:105-107 (1983).
Morissette, S.L. et al., "High-throughput crystallization:polymorphs, salts, co-crystals and solvates of pharmaceutical solids," *Advanced Drug Delivery Reviews*, 56:275-300 (2004).
Murase, K., et al., "New β-adrenoreceptor stimulants. Studies on 3-acylamino-4-hydroxy-α-(N-substituted aminomethyl)benzyl alcohols," *Chem. Pharm. Bull.*, 25(6):1368-1377 (1977).
Nielsen, K.G. et al., "Flow-dependent effect of formoterol dry-powder inhaled from the aerolizer®," *Eur. Respir. Journal*, 10:2105-2109 (1997).
Notice of Allowance dated Jan. 26, 2011 in U.S Appl. No. 11/920,561.
Office Action for U.S. Appl. No. 11/920,561, dated Jun. 2, 2010.
Office Action (Quayle Action) for U.S. Appl. No. 11/920,561, dated Nov. 9, 2010.
Office Action for U.S. Appl. No. 12/745,195, dated Mar. 9, 2011.
Office Action for U.S. Appl. No. 12/298,131, dated Apr. 25, 2011.
Office Action for U.S. Appl. No. 12/745,195, dated Jul. 15, 2011.
Office Action for U.S. Appl. No. 12/444,935, dated Jul. 7, 2011.
Office Action for U.S. Appl. No. 12/526,090, dated Oct. 14, 2011.
Patani, G.A. et al., "Bioisosterism: a rational approach in drug design," *Chem. Rev.*, 96:314-3176 (1996).
Portoghese, P.S., "Stereochemical studies on medicinal agents. 19. X-ray crystal structures of two (‡)allylprodine diastereomers. The role of the allyl group in conferring high stereoselectivity and potency at analgetic receptors," *Journal of Medicinal Chemistry*, 19(1):55-57 (1976).
Restriction Requirement for U.S. Appl. No. 11/920,561, dated Mar. 16, 2010.
Restriction Requirement for U.S. Appl. No. 12/745,195, dated Jan. 5, 2011.
Restriction Requirement for U.S. Appl. No. 12/444,935, dated May 13, 2011.
Restriction Requirement for U.S. Appl. No. 12/526,090, dated Jul. 20, 2011.
Silverman, R.B., "The organic chemistry of drug design and drug Action," *Academic Press*, 2:10-23 (1992).
Smart, B.E., "Fluorine substituent effects (on bioactivity)," *Journal of Fluorine Chemistry*, 109:3-11 (2001).
Sterling, J. et al., "Novel dual inhibitors of AChE and MAO derived from hydroxy aminoindan and phenethylamine as potential treatment for alzheimer's disease," *J. Med. Chem.*, 45(24):5260-5279 (2002).
STN Search Report, Accession No. 2003:875242, CAS RN 620599-83-9 (2011).
Svenson, R. et al., "On the hydrozirconation of some long-chain unsaturated fatty acid oxazolines," *Chemica Scripta.*, 19:149-153 (1982).
Vippagunta, S.R. et al., "Crystalline solids," *Advanced Drug Delivery Reviews*, 48:3-26 (2001).
Williams, D.A. et al., *FOYE's Principles of Medicinal Chemistry*, 5th Edition, pp. 59-63 (2002).

Yang, Z. et al., "A novel and practical method for the preparation of α,α-difluoro functionalized esters," *J. Chem. Soc., Chem. Commun.*, 3: 233-234 (1992).
Yang, Z., "Synthesis of new α,α, β,β-tetrafluoroesters," *Journal of Fluorine Chemistry*, 125:763-765 (2004).
Yoshizaki, S. et al., "Sympathomimetic amines having a 3,4-dihydrocarbostyril nucleus," *Chemical and Pharmaceutical Bulletin*, 26(5):1611-1614 (1978).
Yoshizaki, S. et al., "Sympathomimetic amines having a carbostyril nucleus," *Journal of Medicinal Chemistry*, 19(9):1138-1142 (1976).
Dexamethasone, Merck Index, Monograph No. 02943 (2011).
International Search Report mailed Sep. 16, 2010, for International Application No. PCT/EP2010/001582 (WO 2010/102831).
U.S. Appl. No. 13/255,261, filed Sep. 9, 2011, Marchueta Hereu et al.
DeVries, F. et al. "Use of β2 Agonists and Rsk of Acute Myocardial Infarction in Patients with Hypertensionn," Brit. J, Clin. Pharmacol. 65:580:586, 2008.
Salpeter, S.R. et al. "Cardiovascular Effects of β-Agonists in Patients with Asthma and COPD: A Meta-Analysis" Chest 125:2309-2321 (2004).
U.S. Appl. No. 13/202,020: Restriction Requirement dated Oct. 2, 2012.
U.S. Appl. No. 13/202,020; Office Action dated Apr. 8, 2013.
U.S. Appl. No. 13/202,025: Restriction Requirement dated Oct. 4, 2012.
U.S. Appl. No. 13/202,025: Office Action dated Apr. 17,2013.
U.S. Appl. No. 13/255,621: Notice of Allowance dated May 10, 2013.
Bastin, R. J. et al,, "Salt selection and optimisation procedures for pharmaceutical new chemical entities," *Organic Process Research and Development*, 4(5):427-435 (2000).
CAPLUS English Abstract of DE 2 236 272, Accession No. 1973:405128, 1973.
CAPLUS English Abstract of DE 2 310 140, Accession No. 1975:31115, 1975.
CAPLUS English Abstract of JP 51 149 282, Accession No. 1977:468184, 1977.
CAPLUS English Abstract of JP 59 093 051, Accession No. 1985:45790, 1985.
Caplus English Abstract of journal article by Meglio, P. et al. Accession No. 1980:426036, 1980.
Coleman, R.A. et al., "Novel and versatile superfusion system," *Journal of Pharmacological Methods*, 21:71-86 (1989).
Cortijo, J. et al., "Effects of dantrolene on the responses to methylxanthines in the isolated guinea-pig trachea," *European Journal of Pharmacology*, 198:171-176 (1991).
Curran, P.K. et al., "Endogenous β3-but not β1-adrenergic receptors are resistant to agonist-mediated regulation in human SK-N-MC neurotumor cells," *Cell, Signa.*, 8(5):355-364 (1996).
Deyrup, M.D. et al., "Structure-affinity profile of 8-hydroxycarbostyril-based agonists that dissociate slowly from the β2-adrenoceptor," *Naunyn-Schmiedeberg's Archives of Pharmacology*, 359-168-177 (1999).
English Abstract of WO 2002/92606, dated Nov. 21, 2002.
Furuie, H. et al., "Suppressive effect of novel phosphodiesterase4 (PDE4) inhibitor ONO-6126 on TNF-αrelease was Increased after repeated oral administration in healthy Japanese subjects," *Eur. Resp. Journal*, 22(Supp. 45):Abstract 2557 (2003).
Han, J., "Advances in characerzaton of phamaceutcl hydrates," *Trends in Bio/Pharmaceutical Industry*, 3:25-29 (2006).
Hart, D.J., "A Synthesis of (‡)-gephyrotoxin," *Journal of Organic Chemistry*, 46:3576-3578 (1981).
Hart, D.J. et al., "Total syntheses of di-gephyrotoxin and di-dihydrogephyrotoxln," *J. American Chem. Society*, 105(5):1255-1263 (1983).
Hashima, H. et al.,'Synthesis and biological activities of the marine byrozoan alkaloids convolutamines A, C and F, and lutamides A and C,' *Bioorganic & Medicinal Chemistry*, 8:1757-1766 (2000).
Hett, R. et al., "Enantioselective synthesis of salmeterol via asymmetric borane reduction," *Tetrahedron Letters*, 35(50):9375-9378 (1994).
Hett, R. et al., "Large-scale synthesis of enantio- and diastereomerically pure (R,R)-formoterol," *Organic Process Research & Development*, 2(2):96-99 (1998).

(56) References Cited

OTHER PUBLICATIONS

International Search Report mailed Sep. 12, 2006, for International Application No. PCT/EP2006/004680 (WO 2006/122788 A1).
International Search Report mailed Jun. 21, 2007, for International Application No. PCT/EP2007/003601 (WO 2007/124898 A1).
International Search Report mailed Mar. 19, 2008, for International Application No. PCT/EP2007/008992 (WO 2008/046598 A1).
International Search Report mailed May 28, 2008, for International Application No. PCT/EP2008/000975 (WO 2008/095720).
International Search Report mailed Apr. 21, 2009, for International Application No. PCT/EP2009/001431 (WO 2009/106351).
International Search Report mailed May 7, 2009, for International Application No. PCT/EP2008/009469 (WO 2009/068177).
International Search Report mailed May 25, 2010, for International Application No. PCT/EP2010/001027 (WO 2010/094484).
International Search Report mailed May 27, 2010, for International Application No. PCT/EP2010/001026 (WO 2010/094483).
Interview Summary for U.S. Appl. No. 11/920,561, dated Jun. 11, 2010.
Ismail, F.M.D., Important fluorinated drugs in experimental and clinical use,' *Journal of Fluorine Chemistry*, 118:27-33 (2002).
Johnson, M., "Salmeterol," *Medicinal Research Reviews*, 15(3) 225-257 (1995).
Kaiser, C. et al., "Adrenergic agents. 1.synthesis and potential β-adrenergic agonist activity of some catecholamine analogs bearing a substituted amino functionality in the meta position," *Journal of Medicinal Chemistry*, 17(1): 49-57 (1974).
Kikkawa, H. et al., "Differential contribution of two serine residues of wild type and constitutively active $β_2$-adrenoreceptors to the interaction with $β_2$-selective agonists," *British Journal of Pharmacology*, 121:1059-1064 (1997).
de Meglio, P. et al., "Synthesis and pharmacological study of orclprenaline arid salbutamol derivatives," *Farrnaco, Edizione Scientifica*, 35(3):203-230 (1980).
Meyers, A.I. et al., "Oxazolines. XI. synthesis of functionalized aromatic and aliphatic acids. A useful protecting group for carboxylic acids against grignard and hydride reagents," *Journal of Organic Chemistry*, 39(18) 2787-2793 (1974).

\* cited by examiner

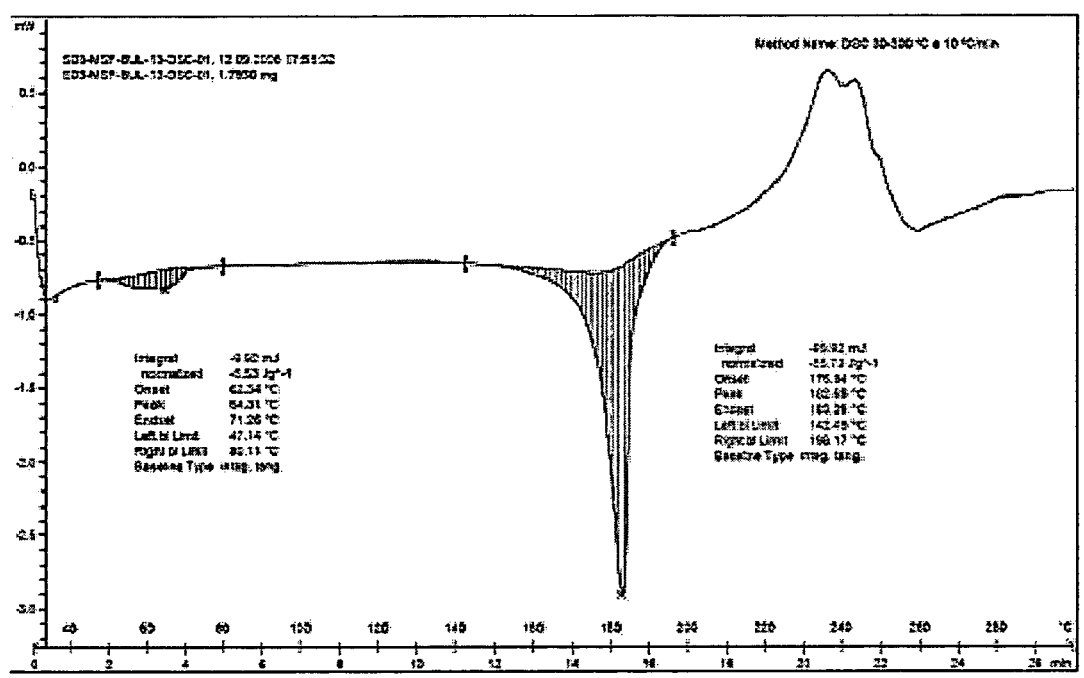

US 8,563,731 B2

MESYLATE SALT OF 5-(2-{[6-(2,2-DIFLUORO-2-PHENYLETHOXY)HEXYL] AMINO}-1-HYDROXYETHYL)-8-HYDROXYQUINOLIN-2(1H)-ONE AS AGONIST OF THE β2 ADRENERGIC RECEPTOR

This application is a national stage filing under 35 U.S.C. §371 of International Application No. PCT/EP2009/008970 filed on 15 Dec. 2009, which claims priority of European Patent Application No. 08382082.9, filed on 22 Dec. 2008. The contents of both applications are incorporated herein by reference.

FIELD OF THE INVENTION

The present invention is directed to novel water-soluble methanesulphonic acid salts (mesylates) of 5-(2-{[6-(2,2-difluoro-2-phenylethoxy)hexyl]amino}-1-hydroxyethyl)-8-hydroxyquinolin-2(1H)-one, its enantiomers and solvates thereof. The invention is also directed to pharmaceutical compositions comprising the salts, methods of using them to treat respiratory diseases susceptible to be ameliorated by β2 adrenergic receptor activity, and processes and intermediates useful for preparing such salts.

BACKGROUND OF THE INVENTION

β2 adrenergic receptor agonists are advantageously administered directly into the respiratory tract by inhalation when used for treating pulmonary or respiratory disorders. Several types of pharmaceutical inhalation devices have been developed for administering therapeutic agents by inhalation including dry powder inhalers (DPI), metered-dose inhalers (MDI) and nebuliser inhalers.

Liquid formulations, in particular aqueous formulations, are easy to administer since they are inhaled during normal breathing through a mouth-piece or a face-mask. They are particularly suitable for young and elderly people who are most often the patients in need of such therapy and who experience difficulties using other devices.

5-(2-{[6-(2,2-difluoro-2-phenylethoxy)hexyl]amino}-1-hydroxyethyl)-8-hydroxyquinolin-2(1H)-one is claimed and described in published patent application WO 2006/122788 A1.

Although 5-(2-{[6-(2,2-difluoro-2-phenylethoxy)hexyl]amino}-1-hydroxyethyl)-8-hydroxyquinolin-2(1H)-one has shown adequate pharmacological behaviour it has proved difficult to obtain it in the form of a salt which is water-soluble and especially very stable when in aqueous solutions.

So far no water-soluble salt of 5-(2-{([6-(2,2-difluoro-2-phenylethoxy)hexyl]amino}-1-hydroxy-ethyl)-8-hydroxyquinolin-2(1H)-one having the desired properties has been reported.

Accordingly, a need exists for a water-soluble and stable salt of this compound which can be used in the preparation of aqueous solutions, particularly suitable for certain patient such us children and the elderly patients.

SUMMARY OF THE INVENTION

It has now been found that methanesulphonic acid salts of 5-(2-{[6-(2,2-difluoro-2-phenylethoxy)hexyl]amino}-1-hydroxyethyl)-8-hydroxyquinolin-2(1H)-one can be obtained in a form of a powder which is very soluble and has a very high stability in aqueous and formulations and thus provides an adequate shelf-life suitable for storage and commercial distribution The present invention provides a mesylate salt of 5-(2-{[6-(2,2-difluoro-2-phenylethoxy)hexyl]amino}-1-hydroxy-ethyl)-8-hydroxyquinolin-2(1H)-one and pharmaceutically acceptable solvates thereof.

The invention also provides a pharmaceutical composition comprising a salt of the invention and a pharmaceutically-acceptable carrier. The invention further provides combinations comprising a salt of the invention and one or more other therapeutic agents and pharmaceutical compositions comprising such combinations.

The invention also provides a method of treating a pulmonary disease or condition susceptible to be ameliorated by β2 adrenergic receptor activity such as asthma or chronic obstructive pulmonary disease, in a mammal, comprising administering to the mammal, a therapeutically effective amount of a salt of the invention. The invention further provides a method of treatment comprising administering a therapeutically effective amount of a combination of a salt of the invention together with one or more other therapeutic agents.

The invention further provides synthetic processes and intermediates described herein, which are useful for preparing salts of the invention.

The invention also provides a salt of the invention as described herein for use in treating a pulmonary disease or condition susceptible to be ameliorated by β2 adrenergic receptor activity such as asthma or chronic obstructive pulmonary disease in a mammal. The invention also provides a method of treatment of these diseases as well as the use of the salt of the invention in the manufacture of a formulation or medicament for treating these diseases.

BRIEF DESCRIPTION OF FIGURES

FIG. 1 shows the DSC pattern of 5-(-2-(6-(2,2-Difluoro-2-phenylethoxy)hexylamino)-1(R)-hydroxyethyl)-8-hydroxyquinolin-2(1H)-one mesylate.

DETAILED DESCRIPTION OF THE INVENTION

When describing the salts, compositions and methods of the invention, the following terms have the following meanings, unless otherwise indicated.

The term "therapeutically effective amount" refers to an amount sufficient to effect treatment when administered to a patient in need of treatment.

The term "treatment" as used herein refers to the treatment of a disease or medical condition in a human patient which includes:
(a) preventing the disease or medical condition from occurring, i.e., prophylactic treatment of a patient;
(b) ameliorating the disease or medical condition, i.e., causing regression of the disease or medical condition in a patient;
(c) suppressing the disease or medical condition, i.e., slowing the development of the disease or medical condition in a patient; or
(d) alleviating the symptoms of the disease or medical condition in a patient.

The phrase "pulmonary disease or condition associated with β2 adrenergic receptor activity" includes all pulmonary disease states and/or conditions that are acknowledged now, or that are found in the future, to be associated with β2 adrenergic receptor activity. Such disease states include, but are not limited to asthma and chronic obstructive pulmonary disease (including chronic bronchitis and emphysema).

The term "solvate" refers to a complex or aggregate formed by one or more molecules of a solute, i.e. a salt of the invention or a pharmaceutically-acceptable salt thereof, and one or more molecules of a solvent. Such solvates are typically crystalline solids having a substantially fixed molar ratio of solute and solvent. Representative solvents include by way of example, water, ethanol, isopropanol and the like. When the solvent is water, the solvate formed is a hydrate.

It will be appreciated that the term "or solvate or stereoisomer thereof" is intended to include all permutations of solvates and stereoisomers, such as a solvate of a stereoisomer of a salt of formula (I).

The salts of the invention contain a chiral center. Accordingly, the invention includes racemic mixtures, enantiomers, and mixtures enriched in one of the enantiomers. The scope of the invention as described and claimed encompasses the racemic forms of the salts as well as the individual enantiomers and enantiomer-enriched mixtures.

Of particular interest are the salts:
(R,S) 5-(2-{[6-(2,2-difluoro-2-phenylethoxy)hexyl]amino}-1-hydroxyethyl)-8-hydroxyquinolin-2(1H)-one, mesylate
5-(2-{[6-(2,2-difluoro-2-phenylethoxy)hexyl]amino}-1(R)-hydroxyethyl)-8-hydroxyquinolin-2(1H)-one, mesylate
and pharmaceutically acceptable solvates thereof.

Most preferably, the salt is 5-(2-{[6-(2,2-difluoro-2-phenylethoxy)hexyl]amino}-1(R)-hydroxy-ethyl)-8-hydroxyquinolin-2(1H)-one mesylate, of formula (I):

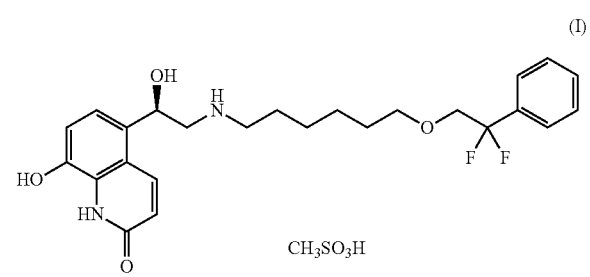 [SMILES: O=c1ccc2c([C@@H](O)CNCCCCCCOCC(F)(F)c3ccccc3)ccc(O)c2[nH]1 ; "CH3SO3H"]

(I)

and pharmaceutically acceptable solvates thereof.

The invention also encompasses pharmaceutical compositions comprising a therapeutically effective amount of a salt as hereinabove defined and a pharmaceutically acceptable carrier.

In an embodiment of the present invention the pharmaceutical composition further comprises a therapeutically effective amount of one or more other therapeutic agents.

It is also an embodiment of the present invention that the pharmaceutical composition is formulated for oral or intravenous administration.

The salts of the present invention as hereinabove defined may also be combined with one or more other therapeutic agents, in particular one or more drugs selected from the group consisting of corticosteroids, anticholinergic agents and PDE4 inhibitors. The invention is also directed to a combination comprising the salt of the invention with one or more other therapeutic agents, in particular one or more drugs selected from the group consisting of corticosteroids, anticholinergic agents and PDE4 inhibitors The invention is also directed to a salt of formula (I) for use in the treatment of a pulmonary disease susceptible to be ameliorated by β2 adrenergic receptor such as asthma or chronic obstructive pulmonary disease.

The invention is also directed to a method of treating a disease or condition in a mammal susceptible to be ameliorated by β2 adrenergic receptor, the method comprising administering to the mammal, a therapeutically effective amount of a pharmaceutical composition comprising a β2 adrenergic receptor agonist according to the present invention. It is of particular relevance the method applied to the treatment of a disease or condition which is a pulmonary disease, preferably asthma or chronic obstructive pulmonary disease.

The invention is also directed to the use of a salt of formula (I) in the manufacture of a medicament for the treatment of a pulmonary disease or condition in a mammal. The mammal is preferably a human being. Particularly relevant pulmonary diseases or conditions are asthma or chronic obstructive pulmonary disease.

General Synthetic Procedures

The salts of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Processes for preparing salts of the invention are provided as further embodiments of the invention and are illustrated by the procedures below.

The salts of the invention can be synthesized from 5-(2-{[6-(2,2-difluoro-2-phenylethoxy)hexyl]amino}-1-hydroxyethyl)-8-hydroxyquinolin-2(1H)-one and from methanesulfonic acid which is commercially available from, for example, Aldrich.

Suitable inert diluents for this reaction include, but are not limited to, acetone, ethyl acetate, dimethylformamide, chloroform, methanol, ethanol, isopropanol, 2-butanol and the like, and mixtures thereof, optionally containing water. For example, the free base can be contacted with methanesulphonic acid, dissolved in 2-butanol Upon completion of any of the foregoing reactions, the salt can be isolated from the reaction mixture by any conventional means such as precipitation, concentration, centrifugation and the like.

It will be appreciated that while specific process conditions (i.e. reaction temperatures, times, mole ratios of reactants, solvents, pressures, etc.) are given, other process conditions can also be used unless otherwise stated.

A water-soluble mesylate salt of the invention typically contains between about 0.85 and 1.15 molar equivalents of methanesulphonic acid per molar equivalent of the free base, more typically about 1 molar equivalent of methanesulphonic acid per molar equivalent of the free base.

The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

To prepare the mesylate salt of the present invention, the free base is typically dissolved in a solvent such as acetone, ethyl acetate, dimethylformamide, chloroform, methanol, ethanol, isopropanol, 2-butanol and mixtures thereof, particularly 2-butanol to form a 0.20-0.25 M solution which is then heated to approximately 60-70° C. Then a solution of 0.45-0.50 M of methanesulphonic acid in an adequate solvent is added dropwise to the heated solution. The mixture is then stirred for 60 minutes at 70-75° C. and then cooled down to 20/25° C. and smoothly stirred overnight. The precipitate formed is isolated by filtration, washed with an appropriate solvent and dried for example in vacuum at 50° C.

EXAMPLES

General. Reagents, starting materials, and solvents were purchased from commercial suppliers and used as received.

A particularly good solvent used to prepare a 5-(2-{([6-(2,2-difluoro-2-phenylethoxy)hexyl]-amino}-1(R)-hydroxyethyl)-8-hydroxyquinolin-2(1H)-one mesylate salt was 2-butanol. The reaction comprised dissolving 11.4 g (24.8 mmols) of free base in 104 ml of 2-butanol to form a 0.24 M solution which was heated to approximately 75° C. Then, a solution of 2.37 g (24.6 mmols) of methylsulphonic acid in 52 ml of 2-butanol were added dropwise during 30 minutes to the heated solution. Once the addition is finished, the mixture was then stirred for 1 hour at 70-75° C. and then cooled down to room temperature and smoothly stirred at this temperature overnight. The precipitate formed was isolated by filtration, washed with 2-butanol (15 ml) and dried in vacuum at 50° C. 10.93 g (yield: 79%) of a white solid was then obtained with a purity of 97.5% by HPLC.

The differential scanning calorimetry (DSC) analysis was obtained using a DSC-821 Mettler-Toledo, serial number 5117423874. Samples were weighed into an aluminium pan, an aluminium lid placed on top of the sample and compressed with a brass rod. Samples were equilibrated at 30° C. and heated at 10° C./min to 300° C. The instrument was calibrated using indium and zinc standards.

FIG. 1 shows a DSC pattern of the salt 5-(-2-(6-(2,2-Difluoro-2-phenylethoxy)hexyl-amino)-1(R)-hydroxyethyl)-8-hydroxyquinolin-2(1H)-one mesylate. The sample exhibits a wide and small endotherm with an onset of around 62° C., and a characteristic high endotherm at onset 183.04° C. that corresponds to a melting or decomposition of the salt. This indicates that the sample does not convert into any other polymorphs and does not suffer any decomposition, confirming thus its high stability.

Water-Solubility Test:

The solubility of different salts of 5-(-2-(6-(2,2-Difluoro-2-phenylethoxy)hexyl-amino)-1(R)-hydroxyethyl)-8-hydroxyquinolin-2(1H)-one in water at room temperature was determined together with the solubility of formoterol fumarate and salmeterol xinofoate. The results are shown in Table 1 below.

| Product | Water Solubility @ 25° C. (mg/ml as Base) |
|---|---|
| Formoterol Fumarate | 1.81 |
| Salmeterol Xinafoate | 0.032 |
| 5-(-2-(6-(2,2-Difluoro-2-phenylethoxy)hexyl-amino)-1(R)-hydroxyethyl)-8-hydroxyquinolin-2(1H)-one napadisylate | 0.018 |
| 5-(-2-(6-(2,2-Difluoro-2-phenylethoxy)hexyl-amino)-1(R)-hydroxyethyl)-8-hydroxyquinolin-2(1H)-one hydrogensulphate | 1.19 |
| 5-(-2-(6-(2,2-Difluoro-2-phenylethoxy)hexyl-amino)-1(R)-hydroxyethyl)-8-hydroxyquinolin-2(1H)-one mesylate | 16.3 |

As it can be seen for the table, the mesylate salt of the present invention presents a higher solubility over the corresponding hydrogensulphonate or napadisylate salt. Moreover the mesylate of the present invention exhibits a higher solubility when compared with formoterol fumarate and salmeterol xinofoate, the two commercially available long-acting β2 agonists.

Stability Test:

Stability of the mesylate salt of the present invention was evaluated under accelerated condition. About 5 mg of the mesylate salt of the present invention were introduced in individual 10 ml amber glass vials. These vials were stored at 40° C. during 30 days and at 80° C. during 15 and 30 days, respectively. After the forced stress conditions, samples were dissolved in 5 ml of the appropriate solvent. Impurities increase was determined using HPLC analysis and by calculating the relative areas. Results are reported in Table 2

TABLE 2

| Data | HPLC Impurities (% area) |
|---|---|
| Stability @ 80° C. 15 days | 3.10% |
| Stability @ 80° C. 30 days | 3.8% |
| Stability @ 40° C. 30 days | 2.4% |

15 days stability at 80° C. indicates an equivalent of more than 1 year at 30° C. 30 days stability at 80° C. indicates an equivalent of more than 1 year at 40° C. The percentage of impurities observed in all forced conditions is less than 5%, thus indicating that there has not been any significant degradation of the salt.

Pharmaceutical Compositions

Pharmaceutical compositions according to the present invention comprise a therapeutically effective amount of a mesylate salt of 5-(2-{[6-(2,2-difluoro-2-phenylethoxy)hexyl]amino}-1-hydroxyethyl)-8-hydroxyquinolin-2(1H)-one or an enantiomer or pharmaceutically acceptable solvate thereof and a pharmaceutically acceptable carrier.

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Dry powder compositions for topical delivery to the lung by inhalation may, for example, be presented in capsules and cartridges of for example gelatine or blisters of for example laminated aluminium foil, for use in an inhaler or insufflator. Formulations generally comprise a powder mix for inhalation of the salt of the invention and a suitable powder base (carrier substance) such as lactose or starch. Use of lactose is preferred. The powder base may include additional components such as preservatives, stabilizing agents, absorption enhancers or aerodynamic modifier.

Each capsule or cartridge may generally contain between 0.1 μg and 150 μg of each therapeutically active ingredient. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (e.g. EP0069715) or disks (e.g. GB 2041763; EP 0424790; DE 4239402 and EP 0674533), rotatable cylinders (e.g. EP 0166294; GB 2165159 and WO 92/09322) and rotatable frustums (e.g. WO 92/00771), all having cavities which have to be filled with powder from the container. Other multi dose devices have measuring plungers with a local or circumferential recess to displace a certain volume of powder from the container to a delivery chamber or an air conduit (e.g. EP 0505321, WO 92/04068 and WO 92/04928), or measuring slides such as the Genuair® devise (formerly knows as Novolizer SD2FL) which is described in the following patent applications: WO 97/000703, WO 03/000325 and WO 03/061742.

A preferred embodiment of the present invention is the use of a liquid formulation comprising the salt of the invention in a device or system suitable for aerosol administration, such as nebulisers or pressurized metered dose inhalers (MDIs). The aerosols may be generated via propellant gases, motor-driven impeller or by means of so-called atomisers, via which the pharmacologically-active substances can be sprayed under high pressure so that, a mist of inhalable particles results. Suitable atomiser may be for example the Respimat® which is described, for example, in W0 91/14468 and WO 97/12687. In case of nebulisers, special nozzles may be used to nebulise the solution such as those described, for example, in WO 94/07607. Nebulisers typically use compressed air, ultrasonic waves, or a vibrating mesh to create a mist of droplets and may also have a baffle to remove larger droplets from the mist by impaction. A variety of nebulisers may be used for this purpose such as ultrasonic nebulisers, jet nebulisers and breath-actuated nebulisers.

The compositions of the invention can optionally comprise a therapeutically effective amount of one or more other therapeutic agents which are known to be useful in the treatment of respiratory disorders, such as PDE4 inhibitors, corticosteroids and/or anticholinergics.

The amount of each active which is required to achieve a therapeutic effect will, of course, vary with the particular active, the route of administration, the subject under treatment, and the particular disorder or disease being treated.

The active ingredients may be administered from 1 to 6 times a day, sufficient to exhibit the desired activity. Preferably, the active ingredients are administered once or twice a day, most preferably once a day.

Examples of suitable PDE4 inhibitors that can be combined with β2-agonists are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, filaminast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N-6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-isopropyl-3H-purine hydrochloride (V-11294A), 643-(N,N-Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl)pyridin-2(1H)-one (1-440), (−)-trans-2-[3'-[3-(N-Cyclopropylcarbamoyl)-4-oxo-1,4-dihydro-1,8-naphthyridin-1-yl]-3-fluorobiphenyl-4-yl]cyclopropanecarboxylic acid (MK-0873), CDC-801, UK-500001, BLX-914, 2-carbomethoxy-4-cyano-4-(3-cyclopropylmethoxy-4-difluororomethoxyphenyl)cyclohexan1-one, cis[4-cyano-4-(3-cyclopropylmethoxy-4-difluoromethoxyphenyl)cyclohexan-1-ol, CDC-801, 5(S)-[3-(Cyclopentyloxy)-4-methoxyphenyl]-3(S)-(3-methylbenzyl)piperidin-2-one (IPL-455903), ONO-6126 (Eur Respir J 2003, 22(Suppl. 45): Abst 2557) and the salts claimed in the PCT patent applications number WO03/097613, WO2004/058729, WO 2005/049581, WO 2005/123693 and WO 2005/123692.

Examples of suitable corticosteroids and glucocorticoids that can be combined with β2-agonists are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, butixocort propionate, RPR-106541, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, 21-Chloro-11beta-hydroxy-17alpha-[2-(methylsulfanyl)acetoxy]-4-pregnene-3,20-dione, Desisobutyrylciclesonide, hydrocortisone acetate, hydrocortisone sodium succinate, NS-126, prednisolone sodium phosphate and hydrocortisone probutate, Prednisolone sodium metasulfobenzoate and clobetasol propionate Examples of suitable M3 antagonists (anticholinergics) that can be combined with β2-agonists are tiotropium salts, oxitropium salts, flutropium salts, ipratropium salts, glycopyrronium salts, trospium salts, zamifenacin, revatropate, espatropate, NPC-14695, BEA-2108, 3-[2-Hydroxy-2,2-bis(2-thienyl)acetoxy]-1-(3-phenoxypropyl)-1-azoniabicyclo[2.2.2]octane salts (in particular aclidinium salts, more preferably aclidinium bromide), 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N—[N-[2-[N-[1-(Cyclohexylmethyl)piperidin-3(R)-ylmethyl]carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), 3(R)-[4,4-Bis(4-fluorophenyl)-2-oxoimidazolidin-1-yl]-1-methyl-1-[2-oxo-2-(3-thienyl)ethyl]pyrrolidinium iodide, N-[1-(3-Hydroxybenzyl)-1-methylpiperidinium-3(S)-yl]-N-[N-[4-(isopropoxycarbonyl)phenyl]carbamoyl]-L-tyrosinamide trifluoroacetate, UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 3(R)-[4,4-Bis(4-fluorophenyl)-2-oxoimidazolidin-1-yl]-1-methyl-1-(2-phenylethyl)pyrrolidinium iodide, trans-4-[2-[Hydroxy-2,2-(dithien-2-yl)acetoxy]-1-methyl-1-(2-phenoxyethyl) piperidinium bromide from Novartis (412682), 7-(2,2-diphenylpropionyloxy)-7,9,9-trimethyl-3-oxa-9-azoniatricyclo[3.3.1.0*2,4]nonane salts, 7-hydroxy-7,9,9-trimethyl-3-oxa-9-azoniatricyclo[3.3.1.0*2,4]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Particularly preferred pharmaceutical composition according to the invention comprise a salt of formula (I) and a therapeutically effective amount of one or more additional therapeutic agents selected from the group consisting of mometasone furoate, ciclesonide, budesonide, fluticasone propionate, fluticasone furoate, tiotropium salts, glycopyrronium salts, 3-[2-Hydroxy-2,2-bis(2-thienyl)acetoxy]-1-(3-phenoxypropyl)-1-azoniabicyclo[2.2.2]octane salts (in particular aclidinium salts, preferably aclidinium bromide), 1-(2-Phenylethyl)-3-(9H-xanthen-9-ylcarbonyloxy)-1-azoniabicyclo[2.2.2]octane salts, rolipram, roflumilast, cilomilast and the compounds claimed in the PCT patent applications number WO03/097613, WO2004/058729, WO 2005/049581, WO 2005/123693 and WO 2005/123692.

Still particularly preferred pharmaceutical composition according to the invention comprise a salt of formula (I) and a therapeutically effective amount of one or more additional therapeutic agents selected from the group consisting of mometasone furoate, ciclesonide, budesonide, fluticasone propionate, fluticasone furoate, tiotropium salts, glycopyrronium salts, 3-[2-Hydroxy-2,2-bis(2-thienyl)acetoxy]-1-(3-phenoxypropyl)-1-azoniabicyclo[2.2.2]octane salts (in particular aclidinium salts, preferably aclidinium bromide), 1-(2-Phenylethyl)-3-(9H-xanthen-9-ylcarbonyloxy)-1-azoniabicyclo[2.2.2]octane salts, rolipram, roflumilast and cilomilast Thus, in one aspect of the invention, the composition comprises a salt of formula (I) and a corticosteroid. Particularly preferred corticosteroids are those selected from the group consisting of mometasone furoate, ciclesonide, budesonide, fluticasone furoate and fluticasone propionate.

In another aspect of the invention, the composition comprises a salt of formula (I) and an anticholinergic agent. Particularly preferred anticholinergic agents are those selected from the group consisting of tiotropium salts, glycopirronium salts, 3-[2-Hydroxy-2,2-bis(2-thienyl)acetoxy]-1-(3-phenoxypropyl)-1-azoniabicyclo[2.2.2]octane salts and 1-(2-Phenylethyl)-3-(9H-xanthen-9-ylcarbonyloxy)-1-azoniabicyclo[2.2.2]octane salts. The composition may further comprise a corticosteroid selected from the group consisting of mometasone furoate, ciclesonide, budesonide, fluticasone furoate and fluticasone propionate.

In a still other aspect of the invention, the composition comprises a salt of formula (I) and a PDE4 inhibitor. Particularly preferred PDE4 inhibitors are those selected from the group consisting of rolipram, roflumilast, cilomilast and the compounds claimed in the PCT patent applications number WO03/097613, WO2004/058729, WO 2005/049581, WO 2005/123693 and WO 2005/123692. The composition may further comprise a corticosteroid selected from the group consisting of mometasone furoate, ciclesonide, budesonide, fluticasone furoate and fluticasone propionate. In addition to the salt of the invention and to the PDE4 inhibitor, the composition may further comprise an anticholinergic agent selected from the group consisting of tiotropium salts, glycopirronium salts, 3-[2-Hydroxy-2,2-bis(2-thienyl)acetoxy]-1-(3-phenoxypropyl)-1-azoniabicyclo[2.2.2]octane salts and 1-(2-Phenylethyl)-3-(9H-xanthen-9-ylcarbonyloxy)-1-azoniabicyclo[2.2.2]octane salts.

In a particularly preferred embodiment of the present invention, the composition comprises a salt of formula (I) and a therapeutically effective amount of a 3-[2-Hydroxy-2,2-bis(2-thienyl)acetoxy]-1-(3-phenoxypropyl)-1-azoniabicyclo[2.2.2]octane salts. Optionally, the composition further comprises a corticosteroid and/or a PDE4 inhibitor.

In another particularly preferred embodiment of the present invention, the composition comprises a salt of formula (I) and a therapeutically effective amount of mometasone furoate. Optionally, the composition further comprises an anticholinergic and/or a PDE4 inhibitor.

In yet another embodiment of the invention, the composition comprises salt of formula (I), a corticosteroid, an anticholinergic agent and a PDE4 inhibitor.

The salts of formula (I) and the combinations of the invention may be used in the treatment of respiratory diseases, wherein the use of bronchodilating agents is expected to have a beneficial effect, for example asthma, acute or chronic bronchitis, emphysema, or Chronic Obstructive Pulmonary Disease (COPD).

The active compounds and the salts in the combination, i.e. the β2-agonist of the invention and the PDE4 inhibitors, corticosteroids or glucocorticoids and/or anticholinergics may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially nebulisers and metered dose inhalers; however, any other form of topical, parenteral or oral application is possible. Here, the application of inhaled compositions embodies the preferred application form, especially in the therapy of obstructive lung diseases or for the treatment of asthma.

The active compound(s) formulations generally contain a suitable carrier which may be either a propellant for MDI administration or water for administration through a nebuliser. The formulation may comprise additional components such as preservatives (for example, benzalkonium chloride, potassium sorbate, benzyl alcohol); pH stabilizers (fro example, acidic agents, alkaline agents, buffer systems); isotonic stabilizers (for example, sodium chloride); surfactant and wetting agents (for example, polysorbates, sorbitan esters); and/or absorption enhancers (for example, chitosan, hyaluronic acid, surfactants). The formulation may also contain additives to improve the solubility of other active compounds when mixed with the salt of the invention. The solubility enhancers may comprise components such as cyclodextrins, liposomes or co-solvents such as ethanol, glycerol and propylene glycol.

Additional suitable carriers for formulations of the active salts of the present invention can be found in Remington: The Science and Practice of Pharmacy, 20th Edition, Lippincott Williams & Wilkins, Philadelphia, Pa., 2000. The following non-limiting examples illustrate representative pharmaceutical compositions of the invention.

The invention further encompasses a method of treating a pulmonary disease or condition, such as asthma or chronic obstructive pulmonary disease in a mammal associated with β2 adrenergic receptor activity, the method comprising administering to the mammal, a therapeutically effective amount of a pharmaceutical composition as described above. The mammal is preferably a human being.

In particular the method of treating a pulmonary disease or condition comprises administering to the mammal, preferably a human being, a therapeutically effective amount of a mesylate salt of a compound of formula (I) and a therapeutically effective amount of one or more other therapeutic agents, such as a corticosteroid, an anticholinergic agent, or a PDE4 inhibitor.

Formulation Example 1

Formulation for a Nebuliser

| Ingredient | Amount |
| --- | --- |
| 5-(2-{[6-(2,2-difluoro-2-phenylethoxy)hexyl]amino}-1(R)-hydroxy-ethyl)-8-hydroxyquinolin-2(1H)-one, mesylate (micronized) | 0.05 µg/ml (equivalent to 1 µg per dosis) |
| sodium chloride (9 mg/ml) | q.s. to 20 ml |

Formulation Example 2

Formulation for a Nebuliser

| Ingredient | Amount |
| --- | --- |
| 5-(2-{[6-(2,2-difluoro-2-phenylethoxy)hexyl]amino}-1(R)-hydroxy-ethyl)-8-hydroxyquinolin-2(1H)-one, mesylate (micronized) | 5 µg/ml (equivalent to 100 µg per dosis) |
| sodium chloride (9 mg/ml) | q.s. to 20 ml |

Formulation Example 3

Formulation for a MDI

| Ingredient | Amount |
| --- | --- |
| 5-(2-{[6-(2,2-difluoro-2-phenylethoxy)hexyl]amino}-1(R)-hydroxy-ethyl)-8-hydroxyquinolin-2(1H)-one, mesylate (micronized) | 0.12 mg (equivalent to 1 µg per dosis) |
| 1,1,1,2-tetrafluoroethane | q.s. to 10 g |

Formulation Example 4

Formulation for a MDI

| Ingredient | Amount |
| --- | --- |
| 5-(2-{[6-(2,2-difluoro-2-phenylethoxy)hexyl]amino}-1(R)-hydroxy-ethyl)-8-hydroxyquinolin-2(1H)-one, mesylate (micronized) | 60 µg (equivalent to 0.5 µg per dosis) |
| 1,1,1,2-tetrafluoroethane | q.s. to 10 g |

The invention claimed is:

1. A mesylate salt of 5-(2-{[6-(2,2-difluoro-2-phenylethoxy)hexyl]amino}-1-hydroxyethyl)-8-hydroxyquinolin-2(1H)-one.

2. The salt according to claim 1, chosen from:
(R,S)5-(2-{[6-(2,2-difluoro-2-phenylethoxy)hexyl]amino}-1-hydroxy-ethyl)-8-hydroxyquinolin-2(1H)-one, mesylate, and 5-(2-{[6-(2,2-difluoro-2-phenylethoxy)hexyl]amino}-1 (R)-hydroxy-ethyl)-8-hydroxyquinolin-2(1H)-one, mesylate.

3. A pharmaceutical composition comprising a therapeutically effective amount of a salt according to claim 1 and a pharmaceutically acceptable carrier.

4. The pharmaceutical composition according to claim 3, wherein the composition is formulated for administration by inhalation.

5. The pharmaceutical composition according to claim 3, wherein the composition further comprises a therapeutically effective amount of at least one other therapeutic agent.

6. The pharmaceutical composition according to claim 5, wherein the at least one other therapeutic agent is chosen from corticosteroids, anticholinergic agents, and PDE4 inhibitors.

7. The pharmaceutical composition according to claim 5, wherein the at least one other therapeutic agent is a corticosteroid chosen from prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, butixocort propionate, (20R)-16α,17α-butylidenedioxy-6α,9α-difluoro-11β-hydroxy-17β-(methylthio)androst-4-en-3-one, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, 21-Chloro-11beta-hydroxy-17alpha-[2-(methylsulfany)acetoxy]-4-pregnene-3,20-dione, Desisobutyrylciclesonide, desisobutyrylciclesonide, hydrocortisone acetate, hydrocortisone sodium succinate, 9-fluoro-11β,17,21-trihydroxy-16α-methylpregna-1,4-diene-3,20-dione 21-cyclohexanecarboxylate 17-cyclopropanecarboxylate, prednisolone sodium phosphate, hydrocortisone probutate, prednisolone sodium metasulfobenzoate, and clobetasol propionate.

8. The pharmaceutical composition according to claim 5, wherein the at least one other therapeutic agent is an anticholinergic agent chosen from tiotropium salts, oxitropium salts, flutropium salts, ipratropium salts, glycopyrronium salts, trospium salts, zamifenacin, revatropate, espatropate, 3-(4-Benzylpiperazinyl)-1-cyclobutyl-1-hydroxy-1-phenyl-2-propanone, di-(2-thienyl)-glycolic acid tropenol ester, 3-[2-Hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N-[N-[2-[N-[1-(Cyclohexylmethyl)piperidin-3(R)-ylmethyl] carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), 3(R)[4,4-Bis(4-fluorophenyl)-2-oxoimidazolidin-1-yl]1-methyl-1-[2-oxo-2-(3-thienyl)ethyl]pyrrolidinium iodide, N-[1-(3-Hydroxybenzyl)-1-methylpiperidinium-3(S)-yl]-N-[-N-[4-(isopropoxycarbonyl)phenyl]carbamoyl]-L-tyrosinamide trifluoroacetate, 6-(azepan-1-yl)-N,2-dicyclopropyl-5-methylprimidin-4-amine, 7-endo-(2-hydroxy-2,2-diphenylacetoxy)-9,9-dimethyl-3-oxa-9-azoniatricyclo[3.3.1.0(2,4)] nonane salts, 3(R)-[4,4-Bis(4-fluorophenyl)-2-oxoimidazolidin-1-yl]-1-methyl-1-(2-phenylethyl) pyrrolidinium iodide, trans-4-[2-[Hydroxy-2,2-(dithien-2-yl)acetoxy]-1-methyl-1-(2-phenoxyethyl) piperidinium bromide, 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts.

9. The pharmaceutical composition according to claim 5, wherein the at least one other therapeutic agent is a PDE4 inhibitor chosen from benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, filaminast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine (NCS-613), N-(3,5-Dichloro-4-pyridinyl)-8-methoxyquinoline-5-carboxamide (D-4418), N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-(ethylamino)-8-isopropyl-3H-purine hydrochloride (V-11294A), 6-[3-(N,N-Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl) pyridin-2(1H)-one(T-440), (-)-trans-2-[3'-[3-(N-Cyclopropylcarbamoyl)-4-oxo-1,4-dihydro-1,8-naphthyridin-1-yl]-3-fluorobiphenyl-4-yl] cyclopropanecarboxylic acid (MK-0873), 2-carbomethoxy-4-cyano-4-(3-cyclopropylmethoxy-4-difluoromethoxyphenyl)-cyclohexan-1-one, cis[4-cyano-4-(3-cyclopropylmethoxy-4-difluoromethoxyphenyl)-cyclohexan-1-ol, and 5(S)[3-(Cyclopentyloxy)-4-methoxyphenyl]-3(S)-(3-methylbenzyl)piperidin-2-one (IPL-455903).

10. The pharmaceutical composition according to claim 5, wherein the at least one other therapeutic agent is chosen from mometasone furoate, ciclesonide, budesonide, fluticasone propionate, fluticasone furoate, tiotropium salts, glycopyrrolium salts, 3-[2-Hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo[2.2.2]octane salts, rolipram, roflumilast and cilomilast.

11. A mesylate salt of (5-(2-{[6-(2,2-difluoro-2-phenylethoxy)hexyl]amino}-1(R)-hydroxy-ethyl)-8-hydroxyquinolin-2(1H)-one.

12. A pharmaceutical composition comprising a therapeutically effective amount of a salt according to claim 11 and a pharmaceutically acceptable carrier.

* * * * *

UNITED STATES PATENT AND TRADEMARK OFFICE
CERTIFICATE OF CORRECTION

PATENT NO. : 8,563,731 B2  
APPLICATION NO. : 13/141156  
DATED : October 22, 2013  
INVENTOR(S) : Francesc Carrera Carrera et al.

Page 1 of 1

It is certified that error appears in the above-identified patent and that said Letters Patent is hereby corrected as shown below:

Title page, item (54), and in the Specification, Col. 1, the title of the invention, "MESYLATE SALT OF 5-(2-{[6-(2,2-DIFLUORO-2-PHENYLETHOXY)HEXYL]}AMINO}-1-HYDROXYETHYL)-8-HYDROXYQUINOLIN-2(1H)-ONE AS AGONIST OF THE BETA2 ADRENERGIC RECEPTOR" should read --MESYLATE SALT OF 5-(2-{[6-(2,2-DIFLUORO-2-PHENYLETHOXY)HEXYL]AMINO}-1-HYDROXYETHYL)-8-HYDROXYQUINOLIN-2(1H)-ONE AS AGONIST OF THE BETA2 ADRENERGIC RECEPTOR--.

In the Claims

In Claim 7, col. 13, line 35,

"11beta-hydroxy-17alpha-[2-(methylsulfany)acetoxy]-4-" should read

--11beta-hydroxy-17alpha-[2-(methylsulfanyl)acetoxy]-4- --.

Signed and Sealed this  
Eleventh Day of March, 2014

Michelle K. Lee  
*Deputy Director of the United States Patent and Trademark Office*